United States Patent [19]

Yan

[11] Patent Number: 4,705,909

[45] Date of Patent: Nov. 10, 1987

[54] PROCESS FOR THE SEPARATION OF PARA-XYLENE

[75] Inventor: Tsoung-Y Yan, Philadelphia, Pa.

[73] Assignee: Mobil Oil Corporation, New York, N.Y.

[21] Appl. No.: 833,695

[22] Filed: Feb. 27, 1986

[51] Int. Cl.$^4$ .................................................. C07C 7/12
[52] U.S. Cl. .............................. 585/828; 208/310 Z; 585/820
[58] Field of Search .................... 208/310 Z; 585/820, 585/828

[56] References Cited

U.S. PATENT DOCUMENTS

| | | | |
|---|---|---|---|
| 2,818,449 | 12/1957 | Christensen et al. | 208/310 Z |
| 2,886,509 | 5/1959 | Christensen et al. | 208/310 Z |
| 3,420,772 | 1/1969 | Eck et al. | 208/310 Z |
| 3,422,004 | 1/1969 | Padrta | 208/310 Z |
| 3,531,400 | 9/1970 | Wenner | 208/310 Z |
| 3,622,506 | 11/1971 | de Rosset | 208/310 Z |
| 3,686,342 | 8/1972 | Neuzil | 208/310 Z X |
| 3,732,326 | 5/1973 | Chen | 208/310 Z |
| 3,895,080 | 7/1975 | Davis | 208/310 Z |
| 4,444,986 | 4/1984 | Dessau | 208/310 Z |

*Primary Examiner*—Andrew H. Metz
*Assistant Examiner*—Glenn Caldarola
*Attorney, Agent, or Firm*—Alexander J. McKillop; Michael G. Gilman; Charles J. Speciale

[57] ABSTRACT

The separation of para-xylene from a mixture of $C_8$ aromatic isomers in a zeolite adsorption process is improved by use of water as the desorbent. Increased desorption efficiency is obtained by the addition to the water of small amounts of a $C_1$ to $C_8$ alcohol, an anionic surfactant, an alkali solution or a mixture thereofs. Separation of water from the para-xylene product and raffinate is accomplished by phase separation.

13 Claims, No Drawings

PROCESS FOR THE SEPARATION OF PARA-XYLENE

BACKGROUND OF THE INVENTION

1. Field of the Invention

The present invention relates to an improved process for the separation of xylene isomers. Further, this invention relates to an improved method of separating para-xylene from $C_8$ aromatic mixtures by the use of an immiscible solvent.

2. Discussion of the Prior Art

Para-xylene because of its utilization in the production of terephthalic acid and dimethylterephthalate, both of which are converted into polyester fiber and film, is the $C_8$ aromatic isomer currently in greatest demand. The other xylene isomers are also of some economic importance but are in less demand as chemical intermediates. Thus, while ortho-xylene, meta-xylene, and ethylbenzene are used in the production of phthalic anhydride, isophthalic acid, and styrene, respectively, these isomers are more typically isomerized to produce additional amounts of the more desired para-xylene.

A typical $C_8$ aromatic feedstock which contains all of the $C_8$ aromatic isomers in varying quantities is not readily separated by fractional distillation into all of the individual isomers. Ortho-xylene, which has a boiling point 3.5° C. higher than that of its closest boiling $C_8$ aromatic isomer (meta-xylene), can be separated by conventional fractional distillation techniques. Such ortho-xylene towers will contain 100 to 150 trays and will operate with about a 5–8 to 1 reflux ratio. Ethylbenzene can be separated with increased difficulty from such a $C_8$ aromatic mixture but only by more intricate superfractionation since the boiling point is within 2.2° C. of the boiling point of para-xylene. Typical ethylbenzene fractionators contain 300 to 400 actual trays and require about a 25–50 to 1 reflux to feed ratio. Since the meta and para-xylene differ by only 0.7° C. in boiling point, separation of these isomers by distillation is essentially impossible and other means have to be employed.

Although selected sulfonation and $HF$-$BF_3$ processing schemes have been employed for separating para and meta-xylene, the most commonly encountered commercial technique for separating meta and para-xylene is fractional crystallization, a separation method well known to the art. Unfortunately, complete recovery of high purity para-xylene from a given feed stream is impossible by fractional crystallization because of the eutectic formed between meta-xylene and para-xylene. In fact, 98+ percent purity para-xylene can be recovered from typically encountered refinery streams in only about 60 percent para-xylene recovery per pass through the crystallization zone.

It is to such a separation as this, that selective adsorption techniques are well suited and, indeed, adsorption techniques utilizing crystalline aluminosilicates have been used successfully to separate meta and para-xylene. U.S. Pat. Nos. 3,133,126 and 3,114,782 to Fleck; U.S. Pat. Nos. 3,558,730, 3,558,732, 3,626,020, 3,663,638 to Neuzil and U.S. Pat. No. 3,665,046 to DeRosset and U.S. Pat. No. 3,668,266 to Chen. et al. are illustrative examples. Selective adsorption has the advantage of being able to produce high purity para-xylene in higher yields (about 85–90 percent or higher) than those obtainable by fractional crystallization.

In a particular selective adsorption process, such as that described in U.S. Pat. Nos. 3,558,730, 3,558,732, 3,626,620, 3,663,638 and 3,665,046 a feed mixture containing $C_8$ aromatic isomers contacts a bed of crystalline alumino-silicate adsorbent to effect the selective adsorption of a first $C_8$ aromatic component. A raffinate stream comprising less selectively retained xylene-isomers is withdrawn from the adsorbent bed. The adsorbent bed then is contacted with a desorbent material to remove the selectively adsorbed first $C_8$ aromatic component from the adsorbent, and the desorbed $C_8$ aromatic in admixture with desorbent is withdrawn from the adsorbent mass. The desorbent is then fractionated from the raffinate and extract streams for subsequent reuse in the process. The selectively adsorbed isomer is usually para-xylene.

The most commercially used process, "UOP's Parex Process," is based on a continuous selective adsorption in the liquid phase, employing a fixed bed of solid adsorbent. This solid adsorbent, made from zeolite material that has undergone exchange with barium and potassium, permits entry into the pore structure of the main feed components. The desorbent employed is neither weakly nor strongly adsorbed with respect to the $C_8$ aromatic feed components. Preferred desorbents are toluene or paradiethylbenzene either of which can be readily recovered by distillation from the para-xylene. The open structure of the solid adsorbent, exposing a relatively large surface area to the feed, gives access to more adsorptive sites than if the adsorption were limited to the exterior surface. Para-xylene is the most readily absorbed material. The desorbing liquid can be readily separated from the feed components by distillation. The desorbent is adsorbed by the adsorbent to about the same extent as the feed hydrocarbons. It must be capable of being desorbed by feed hydrocarbons which it displaces by mass action. The continuous process operates with a fixed bed, which appears to move in the opposite direction from the liquid streams.

It is therefore one object of the present invention to provide an improved method of separation of liquid mixtures.

It is another object of this invention to provide an improved process for the separation of para-xylene from $C_8$ mixtures.

A further object of the invention is to improve the economics of a known separation process by the use of a solvent immiscible with the products and the feed so to eliminate the need of distillation.

A still further object of this invention is to use a solvent in order to alleviate air and waste pollution.

The achievement of these and other objects will be apparent from the following description of the subject invention.

SUMMARY OF THE INVENTION

These and other objects are achieved herein by employing an immiscible solvent, such as water, for the separation of a xylene isomer in a zeolite adsorption separation process. The use of water as the desorbent allows the recovery of para-xylene in a xylene adsorption process without employing a distillation step.

In particular, this invention relates to an improvement in an adsorptive-separation process for the separation of para-xylene from a hydrocarbon feed comprising a mixture of $C_8$ aromatic isomers which process comprises the steps of:

(a) contacting said hydrocarbon feed, at less than equilbrium adsorption conditions and in the simultaneous presence of a hereinafter specified desorbent with a bed of crystalline aluminosilicate adsorbent, which is effective for selectively adsorbing a $C_8$ aromatic isomer from a mixture of at least two $C_8$ aromatic isomers, thereby adsorbing a selectively adsorbed component of the feed within said adsorbent, said adsorbent having been subjected prior to step (a) to at least one cycle of steps (a) to (d) herein, said less than equilibrium adsorption conditions being further characterized in allowing a competitive adsorption between said desorbent and said selectively adsorbed feed component for the adsorptive sites on the adsorbent whereby desorbent remains within the adsorbent for the duration of this step (a);

(b) withdrawing from said bed of adsorbent a raffinate stream comprising desorbent and less selectively adsorbed components of the feed;

(c) contacting the adsorbent bed with said desorbent at desorption conditions to effect displacing said selectively adsorbed component of the feed from said adsorbent; and (d) withdrawing from the adsorbent bed an extract stream comprising desorbent and said selectively adsorbed component of the feed;

the improvement which comprises employing water as said desorbent.

DESCRIPTION OF THE INVENTION

In accordance with the present invention, it has been unexpectedly found that the separation of para-xylene from $C_8$ aromatic mixtures can be accomplished by the use of water as the desorbent in a prior art selective adsorption process which employs a zeolite adsorbent.

The process is particularly useful when the zeolite is more hydrophobic in nature. The hydrophobicity of the zeolite can be controlled by changing its $SiO_2/Al_2O_3$ mole ratio. The higher the $SiO_2/Al_2O_3$, the more hydrophobic, the zeolite surface is. When the $SiO_2/Al_2O_3$ ratio exceeds 50, the zeolite starts to exhibit a hydrophobic nature. The other approach to control the hydrophobicity of the zeolite is to treat it with silicone compounds, such as silane, or fluorine compounds.

The conventional separation of para-xylene from $C_8$ aromatics involves two steps:

1. Contacting the feed stream with an adsorbent selective for para-xylene from the $C_8$ aromatics and;

2. Separating the adsorbent from the feed stream and contacting it with a desorbent to recover para-xylene from the adsorbent.

When practicing the present invention, water can be separated from the para-xylene product and raffinate merely by phase separation without the use of thermal energy. The use of water as the desorbent eliminates the conventional step of distillation and makes the improved process of the present invention more economical without a reduction in the overall yield of para-xylene. Further, the elimination of the distillation step substantially reduces environmental pollution caused by the prior art separation process.

In the subject process, the hydrophobicity of the zeolite is critical. When the zeolite is too low in hydrophobicity, i.e., too hydrophilic, the water is very effective for desorbing the selectivity adsorbed p-xylene, but it is too difficult for p-xylene to displace it in the next adsorption cycle leading to early breakthrough of p-xylene and reduced p-xylene recovery. On the other hand, when the zeolite is too hydrophobic, it adsorbs p-xylene selectively and effectively but it is difficult to elute with water because water is not adsorbed by the zeolite strongly enough.

Thus, the hydrophobicity of zeolite has to be controlled. Zeolites which are suitable for use in the subject invention have a $SiO_2/Al_2O_3$ mole ratio of about 25 to about 1000 with a $SiO_2/Al_2O_3$ mole ratio of about 50 to about 1000 being preferred. The zeolites with higher hydrophobicity can be obtained by increasing the $SiO_2/Al_2O_3$ mole ratio.

The hydrophobicity of the zeolites can be increased by treatments with silicone compounds, such as silane and silicone alkyl oxides, and fluorine compounds, such as HF.

The hydrophobicity of the zeolite surface can be modified with other additives to reach an optimum balance, such as light alcohols, anionic sulfonates, caustics and their mixtures.

In one preferred embodiment of this invention, the desorption efficiency of water can be improved by the addition of a small quantity of $C_1$ to $C_8$ alcohol to the water desorbent. The addition of light alcohols increases efficiency when added to the solution in concentrations of about 1 p.p.m. to about 1000 p.p.m., preferably about 10 p.p.m. to about 100 p.p.m.

In another preferred embodiment of this invention, anionic surfactants increase the desorption efficiency of water when added to the water in a concentration range of about 1 p.p.m. to about 100 p.p.m., preferably about 5 p.p.m. to about 50 p.p.m. A wide range of various anionic surfactants, such as for example, alkyl sulfonates can be usefully employed to improve the efficiency of the water as the desorbent.

Other anionic surfactants that can be employed in the present invention to improve the desorption efficiency of water include: polyethoxycarboxylates represented by the general structural formula $R[OCH_2CH_2]_n$, N-acyl-sarcosinates represented by the general structural formula $RCON(CH_3)CH_2CO_2M$; acylated protein hydrolysates; alkylbenzenesulfonates represented by the structural formula $RC_6H_4SO_3M$; napthalenesulfonates represented by the general structural formula $RC_{10}H_6SO_3Na$; -olefinsulfonates represented by the general structural formula $RCH=CHSO_3Na$; dialkyl sulfosuccinates represented by the general formula $RO_2CCH_2(SO_3Na)CO_2R$; sodium N-acyl-N-alkyltaurates represented by the general formula $RCONR^1CH_2CH_2SO_3Na$ ($RCO=Acyl_1R^1$ Alkyl); alkyl sulfates represented by the general structural formula $ROSO_3M$; alcohols, ethoxylated and sulfated, represented by the general structural formula $R[OCH_2CH_2]_nOSO_3M$. Table One below provides a listing of some specific anionic surfactants that can be used in the present invention to improve the efficiency of the water desorbent.

TABLE I

| Polyethoxycarboxylates, $R[OCH_2CH_2]_nCH_2CO_2M$ | | |
| --- | --- | --- |
| Trade name | R | n |
| Sandopan DTC | tridecyl[b] | 7 |
| Sandopan KST | cetyl | 12 |
| Sandopan TA-10 | isostearyl | 5 |
| Sandopan MS-40 | nonylphenyl[b] | 20 |
| N—Acylsarcosinates, $RCON(CH_3)CH_2CO_2M$ | | |
| Trade name | RCO— | M |
| Amposyl C | cocoyl | H |
| Amposyl C-30 | cocoyl | Na |

TABLE I-continued

| Trade name | Fatty acid | Cation |
|---|---|---|
| Amposyl L | lauroyl | H |
| Amposyl L-30 | lauroyl | Na |
| Amposyl O | oleoyl | H |
| Aprosyl 30 | lauroyl | Na |
| Arkosyl LC | cocoyl | Na |
| Arkosyl O | oleoyl | Na |

Acylated Protein Hydrolysates

| Trade name | Fatty acid | Cation |
|---|---|---|
| Maypon 4C | coco | K |
| Maypon 4CT | coco | Tea |
| Maypon K | oleic | Na |
| Maypon UD | undecylenic | K |

Alkylbenzenesulfonates, $RC_6H_4SO_3M$

| Trade name | R | M |
|---|---|---|
| Calsoft LAS-99 | alkyl | H |
| Conco AAS-45S | dodecyl | Na |
| Conco AAS-60S | dodecyl | TEA |
| Conco AAS-SPECIAL 3 | dodecyl | IPA |
| Conco 75S | dodecyl | Ca |
| Conoco C-550 | dodecyl | Na |
| Conoco C-560 | dodecyl | Na |
| Conoco C-650 | tridecyl | Na |
| Conoco SA 597 | dodecyl | H |
| Conoco SA 697 | tridecyl | H |
| DDBSA 99-B | $C_{10}$–$C_{13}$ | H |
| Emkal NOBS | nonyl | Na |
| Richonate 60B | dodecyl | Na |
| Richonic Acid B | dodecyl | H |
| Surco DDBSA | dodecyl | H |
| Surco 60T | alkyl | TEA |
| Witconate 1298 | dodecyl | H |
| Witconate 1298 Soft | dodecyl | H |
| Witconate P1059 | dodecyl | AM |

Naphthalensulfonates, $RC_{10}H_6SO_3Na$

| Trade name | R or description |
|---|---|
| Aerosol OS | isopropyl |
| Alkanol XC, solid | |
| Darvan No 1 | $CH_2O$ condensed |
| Daxad 11 | $CH_2O$ condensed |
| Emkal NNS | nonyl |
| Nekal BA-75 | butyl |
| Nekal BA-77 | isopropyl |
| Petro BA | alkyl |
| Tamol SN | $CH_2O$ condensed |

α-Olefinsulfonates, $RCH=CHSO_3Na$

| Trade name | R |
|---|---|
| Bio Terge AS-40 | $C_{10}$–$C_{12}$ |
| Conco AOS-40 | alkyl |
| Conco AOS-90F | alkyl |
| Witconate AOS | $C_{10}$–$C_{12}$ |

Dialkyl Sulfosuccinates, $RO_2CCH_2(SO_3Na)CO_2R$

| Trade name | R |
|---|---|
| Aerosol AY-100 | amyl |
| Aerosol OT | 2-ethylhexyl |
| Alrowet D-65 | octyl |
| Crestopen 5X | octyl |
| Emcol 4500 | octyl |
| Monawet MB-45 | isobutyl |
| Monawet MT-70 | tridecyl |
| Nekal WT 27 | octyl |
| Schercowet DOS-70 | octyl |
| Tex-Wet 1001 | octyl |

Sodium N—acyl-N—alkyltaurates, $RCONR'CH_2CH_2SO_3Na$ (RCO = acyl, R' = alkyl)

| Trade name | RCO— | R' |
|---|---|---|
| Celopon | oleyl | methyl |
| Concogel | oleyl | methyl |
| Cresterge L | oleyl | methyl |
| Igepon TC 42 | cocoyl | methyl |
| Igepon TN 74 | palmitoyl | methyl |
| Igepon T 77 | oleyl | methyl |
| Igepon TK 32 | tall oil | methyl |
| Igepon CN 42 | palmitoyl | cyclohexyl |
| Tergenol S Liq | oleyl | methyl |

Alkylpheonols Ethoxylated and Sulfated, $RC_6H_4(OC_2H_4)_nOSO_3M$

| Trade name | R | n | M |
|---|---|---|---|
| Alipal CO-433 | nonyl | 4 | Na |
| Alipal CO-436 | nonyl | 4 | $NH_4$ |
| Alipal EP-120 | nonyl | 4 | $NH_4$ |
| Cellopal 100 | alkyl | | TEA |
| Concopal SS | alkyl | | $NH_4$ |
| Neutronyx S-60 | nonyl | 4 | $NH_4$ |
| Triton X-301 | actyl | | Na |
| Witcolate D 51-51 | alkyl | | Na |

Alkyl Sulfates, $ROSO_3M$

| Trade name | R | M |
|---|---|---|
| Avirol SL 1000 | lauryl | Na |
| Avirol SA 4106 | 2-ethylhexyl | Na |
| Avirol SA 4110 | 2 decyl | Na |
| Conco Sulfate A | lauryl | NH4 |
| Conco Sulfate P | lauryl | K |
| Conco Sulfate EP | lauryl | DEA |
| Conco Sulfate WR Dry | lauryl | Na |
| Dunponol C | lauryl | Na |
| Emersal 6400 | lauryl | Na |
| Emersal 6434 | lauryl | TEA |
| Emersal 6462 | octyl/decyl | Na |
| Emersal 6465 | 2-ethylhexyl | Na |
| Equex S | lauryl | Na |
| Equex T | lauryl | TEA |
| Maprofix TLS 65 | lauryl | TEA |
| Maprofix MG | lauryl | Mg |
| Richonol A | lauryl | Na |
| Richonol Am | lauryl | $NH_4$ |
| Richonol T | lauryl | TEA |
| Sipex OLS | octyl | Na |
| Sipex TDS | tridecyl | Na |
| Sole Terge TS-2-S | 2-ethylhexyl | Na |
| Standapol A | lauryl | Na |
| Standapol MLS | lauryl | MEA |
| Standapol T | lauryl | TEA |

Alcohols, Ethoxylated and Sulfated, $R[OCH_2CH_2]_nOSO_3M$

| Trade name | R | n | M |
|---|---|---|---|
| Richnol S-1300C | lauryl | | $NH_4$ |
| Richnol S-5260 | lauryl | | Na |
| Sipex EA | lauryl | | $NH_4$ |
| Sipex TDS | tridecyl | | Na |
| Standapol ES-1 | lauryl | | Na |
| Standapol EA-3 | lauryl | | $NH_4$ |
| Standapol EA-40 | myristyl | | Na |
| Steol CS-460 | $C_{12}$–$C_{15}$(linear) | | Na |
| Steol CA-460 | $C_{12}$–$C_{15}$(linear) | | $NH_4$ |
| Sulfotex PAI | caprylyl/capryl | | $NH_4$ |
| Sulfotex PAI-S | caprylyl/capryl | | Na |
| Witcolate AE-3 | $C_{12}$–$C_{15}$(linear) | 3 | N4 |

In yet another preferred embodiment of this invention, an alkali or caustic substance will increase the desorption efficiency of the water desorbent when added to the water in a concentration of about 1 p.p.m. to about 100 p.p.m. to increase the pH of the desorbent to about 7.5 pH to about 9 pH. The preferred concentration of the caustic or alkali substance is about 5 p.p.m. to about 50 p.p.m. with the optimum pH being about 8. NaOH and similar caustic compounds known to the skilled artisan may be utilized when practicing this embodiment of the invention.

Thus, the efficiency of water as the desorbent in the process of the present invention can be increased by the addition of a $C_1$ to $C_8$ alcohol, an alkyl sulfonate, an alkali or caustic substance or mixtures thereof. For example, the addition of a minute quantity of a light alcohol (i.e. a $C_1$ to $C_8$ alcohol) and an alkali substance increases the efficiency of water as the desorbent in the process of this invention.

Alternately, the efficiency of the water as the desorbent can be increased by addition of any mixture of a $C_1$ to $C_8$ alcohol, an anionic surfactant or an alkali or caustic substance. The addition of any of the mixtures increases the efficiency when added to the water in a concentration of about 1 p.p.m. to about 1000 p.p.m., preferably about 10 p.p.m. to about 100 p.p.m.

These three preferred embodiments may be employed in the alternative or in combination. Thus, mixtures of one or more $C_1$ to $C_8$ alcohols, one or more anionic surfactant or one or more caustic substance, alone or in combination with one or both of the other components, may be added to the water desorbent to improve the separation efficiency. Utilizing the effective concentrations provided above for the individual alcohols, surfactants and caustic materials, the skilled artisan can readily determine without an undue amount of experimentation the effective quantities of each to employ when combined with similar additives or with one or both of the other desorption efficiency improvement additives.

The typical p-xylene product of 99.5% purity contains 0.3% ethylbenzene, 0.1% m-xylene, and 0.1% o-xylene. The relatively high content of ethylbenzene is because ethylbenzene is more readily adsorbed than m-xylene or o-xylene. Since benzoic acid, the oxidation product of ethylbenzene, is a chain terminator in the polymerization step to form polyesters, the purity of p-xylene must be slightly higher for material produced by the process than the purity of p-xylene produced by crystallization.

A wide variety of various aluminosilicates can be utilized in the present invention. The term aluminosilicate is meant to include synthetically produced and naturally occurring aluminosilicates. The aluminosilicates intended to be included in the scope of this invention include ZSM-5, ZSM-11, ZSM-35, ZSM-38, chabazite, mordenite, erionite and the like of which ZSM-5 having a silica to alumina mole ratio greater than about 50 is preferred.

The following examples are presented as specific embodiments of the present invention which show some of the unique characteristics of the present invention, but are not to be considered so constituting a limitation on the present invention.

EXAMPLE 1

This example demonstrates the water sorption of the ZSM-5 zeolite. The ZSM-5 zeolite was calcined to 538° C. and then equilibrated at 25° C. and P/po. The absorption data are shown below in Table I.

TABLE I

| Sorption Capacity of ZSM-5 | | | | |
| --- | --- | --- | --- | --- |
| Zeolite | 1 | 2 | 3 | 4 |
| $SiO_2/Al_2O_3$ | 38 | 63 | 520 | 880 |
| $H_2O$ Sorption mg/g | 97 | 80 | 56 | 51 |
| $C_8$ Aromatic sorption, mg/g | 120 | 130 | 150 | 160 |

The data in Table I indicate that water sorption capacity decreases as the $SiO_2/Al_2O_3$ ratio increases, because the zeolite became more hydrophobic. (Compare zeolite 1 to zeolite 4). However, the high water sorption capacities of zeolites 3 and 4 indicate that the affinity between water and ZSM-5 was very significant.

As the hydrophobicity of zeolite increases, the relative adsorption capacity for water decreases. Thus too high hydrophobicity leads to poor desorption efficiency when water is used as the desorbent.

EXAMPLE 2

To a 5.007 gm sample of ZSM-5 zeolite, an excess amount of para-xylene was added. Upon soaking for 30 minutes, the excess para-xylene was drained and the ZSM-5 was vacuum dried at room temperature for 5 minutes. This resulted in 0.9847 gms of para-xylene being adsorbed by the ZSM-5 zeolite. 12.5607 gms of water were added to the para-xylene loaded ZSM-5 zeolite and shaken to promote water and ZSM-5 contact. It was observed that oil drops of para-xylene floated up to the surface which indicated that water was effective in displacing and desorbing para-xylene. The ZSM-5 zeolite was then washed with 5 gms of water to rinse off any para-xylene occluded in the catalyst bed. Upon drying, 7.001 gms of n-hexane was added to the ZSM-5 zeolite to extract any residual para-xylene. The extract was analyzed by gas chromatography and was found to contain 2.15% of para-xylene. The residual para-xylene in the ZSM-5 was $7.001 \times 2.15\% = 0.1505$ gms. Further, calculation indicated that 84.7% of the para-xylene was desorbed by water. $[(0.98475 - 0.1505) \times 100/0.98475 = 84.7\%]$.

Obviously, other modifications and variations of the present invention are possible in light of the above teachings. It is, therefore, to be understood that changes which are within the full intended scope of the invention as defined by the appended claims.

What is claimed is:

1. In an adsorptive-separation process for the separation of para-xylene from a hydrocarbon feed comprising a mixture of $C_8$ aromatic isomers which process comprises the steps of:
    (a) contacting said hydrocarbon feed, at less than equilbrium adsorption conditions and in the simultaneous presence of a hereinafter specified desorbent with a bed of crystalline aluminosilicate adsorbent, which is effective for selectively adsorbing a $C_8$ aromatic isomer from a mixture of at least two $C_8$ aromatic isomers, thereby adsorbing a selectively adsorbed component of the feed within said adsorbent, said adsorbent having been subjected prior to step (a) to at least one cycle of steps (a) to (d) herein, said less than equilibrium adsorption conditions being further characterized in allowing a competitive adsorption between said desorbent and said selectively adsorbed feed component for the adsorptive sites of the adsorbent whereby desorbent remains within the adsorbent for the duration of this step (a);
    (b) withdrawing from said bed of adsorbent a raffinate stream comprising desorbent and less selectively adsorbed components of the feed;
    (c) contacting the adsorbent bed with said desorbent at desorption conditions to effect displacing said selectively adsorbed component of the feed from said adsorbent; and
    (d) withdrawing from the adsorbent bed an extract stream comprising desorbent and said selectively adsorbed component of the feed;
    the improvement which comprises employing water as said desorbent.

2. The process according to claim 1, wherein said hydrocarbon feed comprises para-xylene and at least one other $C_8$ aromatic isomer.

3. The process according to claim 2, wherein the selectivity adsorbed component of the feed is paraxylene.

4. The process according to claim 1, wherein said adsorbent is ZSM-5 having a silica to alumina mole ratio greater than about 50.

5. The process according to claim 1, wherein said desorbent is mixed with a $C_1$ to $C_8$ alcohol.

6. The process according to claim 5, wherein said $C_1$ to $C_8$ alcohol is present in water in a concentration of about 10 p.p.m. to about 100 p.p.m.

7. The process according to claim 1, wherein said desorbent is mixed with an alkyl sulfonate.

8. The process according to claim 7, wherein said alkyl sulfonate is present in water in a concentration of about 5 p.p.m to about 50 p.p.m.

9. The process according to claim 1, wherein said desorbent is mixed with an alkali or caustic substance.

10. The process according to claim 9, wherein said alkali or caustic substance is NaOH.

11. The process according to claim 9, wherein said alkali or caustic substance is present in water in a concentration of about 5 p.p.m. to about 50 p.p.m. to increase the pH of said desorbent to about 8 pH.

12. The process according to claim 1, wherein said desorbent is mixed with a combination of a $C_1$ to $C_8$ alcohol, an alkyl sulfonate or an alkali or caustic substance.

13. The process according to claim 12, wherein said combination is present in a concentration of about 10 p.p.m. to about 100 p.p.m.

* * * * *